United States Patent [19]

Tomita et al.

[11] 4,032,404

[45] June 28, 1977

[54] FERMENTATION PROCESS FOR PRODUCING APRAMYCIN AND NEBRAMYCIN FACTOR V′

[75] Inventors: Koji Tomita, Kawasaki; Hiroshi Tsukiura, Mitaka; Hiroshi Kawaguchi, Tokyo, all of Japan

[73] Assignee: Bristol-Myers Company, New York, N.Y.

[22] Filed: July 14, 1976

[21] Appl. No.: 705,210

[52] U.S. Cl. .............................................. 195/80 R
[51] Int. Cl.² ....................... C12D 9/00; C12D 9/14
[58] Field of Search ......................... 195/80 R, 96

[56] References Cited

UNITED STATES PATENTS 3,853,709  12/1974  Stark .............................. 195/80 R

*Primary Examiner*—Lionel M. Shapiro
*Assistant Examiner*—Robert J. Warden
*Attorney, Agent, or Firm*—David M. Morse

[57] ABSTRACT

A fermentation process is disclosed for preparing the known aminoglycoside antibiotics apramycin and nebramycin factor V′ by culturing *Streptoalloteichus hindustanus* A.T.C.C. 31217, 31218 or 31219. The so-produced nebramycin factor V′ may subsequently be converted to tobramycin by base catalyzed hydrolysis.

22 Claims, No Drawings

FERMENTATION PROCESS FOR PRODUCING APRAMYCIN AND NEBRAMYCIN FACTOR V'

BACKGROUND OF THE INVENTION

1. Field of the Invention

This invention relates to a new microbiological process for preparing the known aminoglycoside antibiotics apramycin, nebramycin factor V' and tobramycin.

2. Description of the Prior Art

Nebramycin complex is a known complex of eight different aminoglycoside antibiotic components (nebramycin factors I, I', II, III, IV, V', VI and VII) which has been prepared by fermentation of *Streptomyces tenebrarius* (American Type Culture Collection — A.T.C.C. 17920 and 17921). The complex and its preparation using the above organism is described in *Antimicrob. Agents and Chemother.*, 1967, pg. 314–348 and in U.S. Pat. No. 3,691,279 (see also U.S. Pat. No. 3,853,709 disclosing preparation of nebramycin factors II and VII by fermentation of *Streptomyces tenebrarius* NRRL 3816, a mutant strain of *Streptomyces tenebrarius* A.T.C.C. 17920.

Nebramycin factor VI, now named tobramycin, is reported in *Antimicrob. Agents and Chemother.*, 1970, pg. 309–313 to have the structure

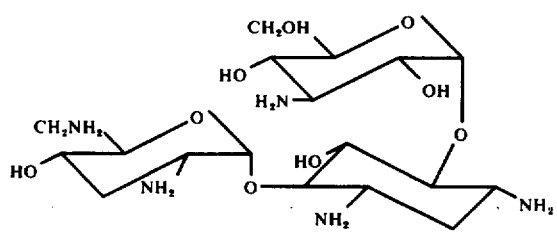

Tobramycin is a commercially available antibiotic which possesses a broad spectrum of antimicrobial activity, including activity against *Pseudomonas* and *Proteus* microorganisms. K. F. Koch, et al. in *J. Antibiotics*, 1973, pg. 745–751 state that tobramycin is not produced directly by fermentation of *Streptomyces tenebrarius* but arises from the acid or base catalyzed hydrolysis of nebramycin factor V' (6''-O-carbamoyltobramycin).

Nebramycin factor II, now named apramycin, is reported in *Annual Reports in Medicinal Chemistry*, Vol. 9, 1974, pg. 99 to have the structure

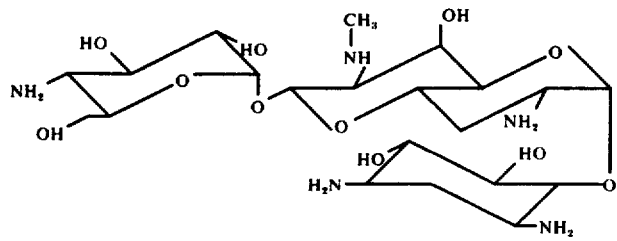

Apramycin is described as being useful as an antimicrobial agent in treating various plant and animal diseases (see U.S. Pat. Nos. 3,691,279, 3,853,709 and 3,876,767).

Nebramine (also called 3'-deoxyneamine or 3'-deoxyneomycin-A) is an aminoglycoside antibiotic which has been prepared by hydrolysis of tobramycin (*Antimicrob. Agents and Chemother.*, 1970, pg. 309–313).

The physical and biological properties of nebramine are disclosed in Belgian Patent 808,393 and in *J. Amer. Chem. Soc.*, Vol. 96, 1974, pg. 3,300–3,305.

Neamine, an aminoglycoside antibiotic degradation product of neomycin, is disclosed in *J. Amer. Chem. Soc.*, Vol. 73, 1951, pg. 2794–2797.

Nebramycin factors IV and V' have been identified as 6''-O-carbamoylkanamycin B and 6''-O-carbamoyltobramycin, respectively. *J. Antibiotics*, Vol. 26, 1973, pg. 745–751.

SUMMARY OF THE INVENTION

The present invention relates to a new microbiological process for the preparation of an aminoglycoside antibiotic mixture comprising the known antibiotics apramycin and nebramycin factor V' by cultivating a strain of *Streptoalloteichus hindustanus* having the identifying characteristics of A.T.C.C. 31217, 31218 or 31219 under submerged aerobic conditions in an aqueous medium containing assimilable sources of carbon and nitrogen until a substantial amount of said antibiotic mixture is produced by said organism in said culture medium and, optionally, recovering the antibiotic mixture from the culture medium.

The invention also provides a process for producing as separate substances the aminoglycoside antibiotics apramycin and nebramycin factor V' by producing an aminoglycoside antibiotic mixture comprising apramycin and nebramycin factor V' by the above-described fermentation procedure, recovering the antibiotic mixture from the culture medium and separating the apramycin and nebramycin factor V' components from the mixture.

A further aspect of the present invention pertains to a process for the preparation of tobramycin by culturing a nebramycin factor V'-producing strain of *Streptoalloteichus hindustanus* having the identifying characteristics of A.T.C.C. 31217, 31218 or 31219 according to the above-described fermentation process until a substantial amount of antibiotic activity is produced by said organism in the culture medium, recovering the so-produced aminoglycoside antibiotic mixture from the culture medium and either (a) separating nebramycin factor V' from said antibiotic mixture and subsequently converting it by base catalyzed hydrolysis to tobramycin or (b) subjecting said antibiotic mixture to base catalyzed hydrolysis to convert the nebramycin factor V' component thereof to tobramycin and separating tobramycin from the resulting antibiotic mixture.

DETAILED DESCRIPTION

The present invention provides a process which comprises fermenting certain strains of *Streptoalloteichus hindustanus*, a heretofore unknown species of microorganism, until an aminoglycoside mixture comprising apramycin and nebramycin factor V' is produced.

The newly found organisms used in this fermentation process are designated herein as *Streptoalloteichus hindustanus* strains C677-91, C801-104 and D251-1. These organisms are actinomycetes bacteria which were isolated from Indian soil samples. Cultures of the organisms have been deposited in the American Type Culture Collection, Washington, D.C., and added to its permanent collection of microorganisms as A.T.C.C. 31217 (strain C677-91), 31218 (strain C-801-104) and 31219 (strain D251-1).

THE MICROORGANISMS

The morphological, cultural and physiological characteristics of strains C677-91, C-b 801-104 and D251-1 are summarized below.

The methods employed for the taxonomic studies of the organisms are those commonly used in the taxonomy of actinomycetes. For morphological observations the organisms were grown at 37° C. on malt extract-yeast extract agar, inorganic salts-starch agar and tyrosine agar. For the formation and observation of sporangium, the organisms were grown at 28° C. for 3-4 weeks on malt extract-yeast extract agar and glycerol asparagine agar. The sporangium and other structures in the vegetative mycelium were investigated by the microscopic observation of thin layer culture prepared by the cover-slip technique described by Kawato and Shinobu in Mem. Osaka Univ. Lib. Arts Educ. 8:114 (1959). The zoospore was liberated from the sporangium into water after immersion for 2-4 hours. The medium and procedures used for the cultural and physiological characterization of the organisms were those recommended by the International Streptomyces Project (SP) in Int. J. Syst. Bacteriol. 16:313-340 (1966). For the carbohydrate utilization test, Pridham and Gottlieb's basal medium was used supplemented with 0.01% Difco yeast extract.

MORPHOLOGY

The actinomycete strain C677-91 produces sporangia singly or collectively in the vegetative hyphae on yeast-extract-malt extract agar and glycerol-asparagine agar. The sporangia are rectangular to subspherical or occasionally spherical in shape, the surface is often uneven and the size of sporangia is 1.5-4.5 by 2.7-7.0 $\mu$m. Peanut shell-shaped sporangium is also formed. Sporangiophores are formed along the surface of agar medium, often with branching and such sporangiophores have a length of 5-20 $\mu$m. Each sporangium contains from one to four or more spores which are arranged in a rod or a v-shaped line. Larger sporangia generally have an empty space. The spores are oval or rod-shaped and the rod-shaped spores are mostly bent and have one or two swellings like a soybean shell. The spores are 0.9-1.5 by 1.2-4 $\mu$m in size and motile with a single polar flagellum which measures 50 $\mu$m or longer.

Strain C677-91 also produces cluster and sclerotium in the aerial mycelium on yeast extract-malt extract agar (ISP No. 2), inorganic salts-starch agar (ISP No. 4) and the other solid media. The cluster is the dominant conidiospore-forming structure and the formation of sclerotia is somewhat capricious. The cluster consists of curved or L-shaped short conidiospore-chains with many branches and often develops into a thick mass. The conidiospore has a smooth surface and is oval to short-cylindrical in shape. Some spore-chains protrude from the cluster structure and often form open spirals. The shape of the sclerotium is oval or occasionally irregular. The aerial mycelial mass consisting of mature spores is liable to be scraped off from the agar surface. The substrate mycelium is branched and not septated and is occasionally twisted and coiled. Globose thick body covered with mycelia is produced which is similar to that reported for the species of genus *Kitasatoa*. It measures 3-20 $\mu$m in diameter.

CULTURAL AND PHYSIOLOGICAL CHARACTERISTICS

Strain C677-91 produces abundant aerial mycelia on most of the agar media tested. The color of the mature aerial mycelium is light yellowish beige or pale pinkish yellow. The substrate mycelium does not have any characteristic color. In case no aerial mycelium is formed, the substrate mycelium penetrates into the agar. Diffusible pigment is not produces. Tyrosinase reaction is negative. Strain C677-91 is thermoduric and grows abundantly at 50° C. The growth is restricted in the agar medium containing 5% NaCl, but no growth is seen at 7% NaCl. It gives normal growth on the Luedemann's potato plug acidity test [Int. J. Syst. Bacteriol. 21:240-247 (1971)]. The cultural and physiological characteristics and the carbohydrate utilization of strain C677-91 are shown in Tables I, II and III, respectively.

TABLE I

Cultural characteristics of strain C677-91

| Medium | | |
|---|---|---|
| Yeast extract-malt extract agar (ISP No. 2 medium) Pridham et al., 1956-57 | G : | Abundant |
| | R : | Pale yellowish brown to light brown |
| | A : | Thick, velvety, light yellowish beige or pale pinkish beige |
| | D : | None |
| Oat meal agar (ISP No. 3 medium) Kuster, 1959 | G : | Moderate |
| | R : | Colorless, partially pale yellowish brown |
| | A : | Powdery to velvety occasionally with patches, pale pinkish beige |
| | D : | None |
| Inorganic salts-starch agar (ISP No. 4 medium) Kuster, 1959 | G : | Moderate |
| | R : | colorless to pale yellowish brown |
| | A : | Powdery to velvety, pale pinkish yellow |
| | D : | None |
| Glycerol-asparagine agar (ISP No. 5 medium) Pridham and Lyons, 1961 | G : | Restricted |
| | R : | colorless to pale olivaceous yellow |
| | A : | Powdery with patches, whitish to pale yellowish beige |
| | D : | None |
| Peptone-yeast extract-iron agar (ISP No. 6 medium) Tresner and Danga, 1958 | G : | Scant |
| | R : | Brown |
| | A: | Scant, white |
| | D : | Pale brown |
| Tyrosine agar (ISP No. 7 medium) Shinobu, 1958 | G : | Moderate |
| | R : | Pale yellow to pale greenish yellow |
| | A : | Velvety to cottony, white later light pinkish yellow |
| | D : | None |
| Bennett's agar | G : | Moderate |
| | R : | Pale olivaceous yellow to light brown |
| | A : | Velvety, light yellowish beige |
| | D : | None |
| Nutrient agar | G : | Restricted |
| | R : | Pale brownish yellow |
| | A : | Scant, white |
| | D : | Pale yellow |
| Soil extract agar | G : | Moderate |
| | R : | Colorless |
| | A : | Thin, pale yellowish beige, patches |
| | D : | None |
| Tomato paste-oat meal agar | G : | Moderate |
| | R : | Light yellowish brown |
| | A : | Velvety, pale pinkish yellow |
| | D : | None |
| Abbreviation : | | G = Growth; R = Reverse color; A = Aerial mycelius; |

TABLE I-continued

Cultural characteristics of strain C677-91

D = Diffusible pigment

TABLE II

Physiological reactions of strain C677-91

| | |
|---|---|
| Gelatin liquefaction | Positive; rapidly liquefied |
| Starch hydrolysis | Positive |
| Milk | Remarkable coagulation and slight peptonization. pH alkalinized. Yellowish ring growth |
| Melanin from L-tyrosine | Negative tyrosinase |
| Nitrite from nitrate | Positive |
| Growth temperature | Abundant growth at 32-50° C, moderate at 25-30° C, restricted at 23° C and 52° C, scant at 20° C and 54° C, no growth at 12° C and 56° C. |
| Fluorescent light | No distinct inhibition of aerial mycelium formation under 15W-fluorescent lamp for 14 days. |
| NaCl tolerance | Restricted growth and restricted aerial mycelium formation in Luedemann's agar medium* in 5% NaCl. No growth at 7% NaCl. |
| Potato plug acidity tolerance | Normal growth and normal aerial mycelium formation on Luedemann's potato plug test* |
| Catalase reaction | Positive |
| Oxidase | Negative |
| Antibiotics produced | Aminoglycoside antibiotic mixture of neamine, nebramine, apramycin and nebramycin factors IV and V'. |

*Int. J. Syst. Bacteriol. 21: 240-247 (1971).

TABLE III

Carbohydrate utilization of strain C677-91

| | | | |
|---|---|---|---|
| Glycerol | ++ | Lactose | ±~+ |
| L-Arabinose | − | Maltose | ++ |
| D-Xylose | − | D-Raffinose | − |
| L-Rhamnose | − | Inositol | − |
| D-Fructose | ++ | D-Mannitol | − |
| D-Galactose | ++ | D-Sorbitol | − |
| D-Glucose | ++ | Cellulose | − |
| D-Mannose | ++ | Inuline | − |
| Sucrose | ±~+ | Salicine | + |

| | |
|---|---|
| Basal agar medium : | Pridham and Gottlieb medium, supplemented with 0.01 % yeast extract. |
| Incubation temperature : | 37° C |

++ : Strongly positive utilization
+ : Positive utilization
± : utilization doubtful
− : Utilization negative

CELL-WALL COMPOSITION

The cell-wall preparation was carried out by the method described by T. Yamaguchi in J. Bacteriol. 89:444-453 (1965). The amino acid analysis procedure was as follows: Purified cell-wall (10 mg.) was hydrolyzed in 1 ml. of 6N HCl in a sealed tube at 120° C. for 18 hours. The hydrolyzate was diluted with an equal volume of distilled water, filtered and then evaporated in vacuo to dryness. Half of the final product was redissolved in 0.1 ml. distilled water and examined by two-dimensional TLC. The other half was dissolved in 2 ml. of citrate buffer (pH 2.2) and analyzed by liquid chromatography. A 5 ul portion of the hydrolyzate was applied to a silica gel TLC plate (60F$_{254}$, E. Merck AG, Germany) and developed with phenol-water (4:1) in one direction and subsequently with n-butanol-acetic acid-water (3:1:1) perpendicularly to the first run. The spots were revealed by a spray of 0.2% ethanolic ninhydrin reagent, followed by heating the plate for 5 minutes at 110° C. Reference standard, a mixture of diaminopimelic acid (DAP), glutamic acid, glycine, alanine, valine and leucine (20 mg./ml. each) was run along with cell-wall sample. In order to differentiate meso and/or DD-DAP from LL-DAP, 5 $\mu$l of the hydrolyzate was applied to a cellulose powder TLC plate. The plate was developed with the solvent system methanol-water-10N HCl-pyridine (80:17.5:2.5:10) for 24 hours and then sprayed with 0.2% ninhydrin reagent In this TLC system, LL-DAP moved faster than the meso-DAP used as a reference standard.

The amino acid composition of the cell-wall preparation was determined according to the above procedure for -en actinomycetes species including strain C677-91, two species of *Nocardia*, two species of *Streptomyces* with ordinary spore-chains, four species of typical cluster-forming *Streptomyces* and *Streptomyces tenebrarius*. The amino acids present were expressed in relative amounts according to the size and intensity of the spots revealed on the TLC plate. The results are summarized in Table IV.

TABLE IV

| | Amino acid composition of cell wall determined by thin layer chromatography | | | | | | |
|---|---|---|---|---|---|---|---|
| | Meso-DAP | LL-DAP | Glycine | Alanine | Glutamic acid | Valine region | Leucine region |
| Strain C677-91 | ++ | − | ± | +++ | ++ | ± | ± |
| Nocardia lutea | ++ | − | − | +++ | ++ | − | − |
| N. corallina | ++ | − | − | +++ | ++ | − | − |
| Streptomyces fradiae | − | ++ | ++ | +++ | ++ | − | − |
| S. kanamyceticus | − | ++ | ++ | +++ | ++ | ± | ± |
| S. massasporeus | − | ++ | ++ | +++ | ++ | ± | ± |
| S. ramulosus | − | ++ | ++ | +++ | ++ | ± | ± |
| S. catenulae | − | ++ | ++ | +++ | ++ | ± | ± |
| S. antimycoticus | − | ++ | ++ | +++ | ++ | ± | ± |
| S. tenebrarius | ++ | − | ± | +++ | ++ | ± | ± |

Alanine and glutamic acid were present in all the actinomycetes strains examined. Glycine was present in all *Streptomyces* strains except *S. tenebrarius*, while its presence was doubtful in strain C677-91 and *S. tenebrarius* and negative in *Nocardia* species. Meso-DAP was present in strain C677-91, two strains of *Nocardia* and *S. tenebrarius*, while LL-DAP was found in all of the reference strains of *Streptomyces* regardless of whether they were of the ordinary spore chain-forming or the cluster-forming type.

The amino acid composition of the cell-wall preparation of strain C677-91 was also examined quantitatively with an amino acid analyzer, comparatively with two reference actinomycetes strains, *N. lutea* and *S. fradiae*. The results are shown in Table V and confirm the findings obtained by the TLC study.

TABLE V

Relative amino acid composition of cell wall determined by amino acid analyzer

| | Strain C677-91 | Nocardia lutea | Streptomyces fradiae |
|---|---|---|---|
| Alanine | 100 | 100 | 100 |
| DAP | 46.9 | 55.8 | 70.6 |
| Glutamic acid | 45.3 | 75.8 | 62.2 |
| Glycine | 4.0 | <2.0 | 68.2 |

The carbohydrate composition of the cell-walls of strain C677-91, N. corallina, S. fradiae, S. antimycoticus and S. tenebrarius was determined as follows: A 50 mg. sample of the crude cell-wall was dissolved in 3 ml. of 2N $H_2SO_4$ and hydrolyzed in a sealed tube at 120°C. for 2 hours. The hydrolyzate was neutralized with saturated $Ba(OH)_2$ solution, the precipitated $BaSO_4$ removed by centrifugation and the supernatant fluid lyophilized. The material thus obtained was trimethylsilylated by the method described in J. Am. Chem. Soc. 85:2497–2507 (1963) and the product subjected to gas chromatography and compared with various reference sugars. The results ae shown in Table VI. Arabinose was found only in the Nocardia species. Galactose and mannose were present in strain C677-91, N. corallina and S. tenebrarius, but not in the other Streptomyces strains. Rhamnose was found in strain C677-91 and S. tenebrarius, but not in Nocardia and two other Streptomyces strains.

phologically typical of those found in some species of Streptomyces or Chainia. The amino acid and sugar composition of the cell-wall preparation of strain C677-91 was quite different, however, from that of any species in the family Streptomycetaceae. Strain C677-91, moreover, produces sporangia in the vegetative mycelium, a characteristic of the family Actinoplanaceae.

Bergey's Manual of Determinative Bacteriology (8th Ed., 1974) describes ten sporangium-forming genera in the family Actinoplanaceae, i.e., Actinoplanes, Ampullaria (Ampullariella), Spirillospora, Streptosporangium and Amorphosporangium [all described by Couch in J. Elisha Mitchell Sci. Soc. 79(1):53–70 (1963)], Pilimelia [J. Elisha Mitchell Sci. Soc. 82:220–230 (1966)], Planomonospora [G. Microbiol. 15:27–38 (1967)], Dactylosporangium [Arch. Mikrobiol. 58:42–52 (1967)] and Kitasatoa ]J. Antibiotics 21:616–625 (1968)]. Comparisons of strain C677-91 with the descriptions of the important genera of Actinoplanaceae are summarized in Table VII.

TABLE VII

Comparison with Genera in Family Actinoplanaceae

| | Shape of sporangia | Arrangement | Sporangiospores Number in a sporangium | Shape | Flagellation | Aerial mycelium | Cell wall type |
|---|---|---|---|---|---|---|---|
| Actinoplanes[1] | Spherical, cylindrical | Coils or rows | Several tens to thousands | Globose, some sub-globose to rod | Lophotrichous or peritrochous | Mostly none or scant | Type II |
| Spirillospora | Spherical to veriform | One or more coils | Several tens to thousands | Short to long rods to spiral | One to three subpolar flagella | White to pale yellow | Type III |
| Streptosporangium | Spherical to ovoid | A single coil | Several tens to thousands | Spherical to ovoid | No flagellum | Abundant | Type III |
| Amorphosporangium | Very irregular | | Several tens to thousands | Rod-shaped | Two or three polar flagella | None | Type II |
| Ampullariella | Much lobed Bottle- or flask-shaped, digitate or lobate | Parallel chains | Several tens to thousands | Rod-shaped | Polytrichous, polar flagella | None | Type II |
| Pilimelia | Large, globose or cylindrical | parallel chains from end to end | Ca. 1,000 | Rod-shaped | Single polar or one to four subpolar or lateral flagella | None | Type IV |
| Dactylosporangium | Finger-shaped usually straight | A single row | Three to five | Rod-shaped | Polytrichous polar flagella | None or rudimentary | Type II |
| Kitasatoa | Club-shaped | A single chain | Single, in pair or in parallel | Diplococcus-like, spherical, ellipsoidal | A single polar flagellum | Abundant | Type I |
| Strain C677-91 | Rectangular, subspherical or spherical | A single rod or V-shaped line | One to four or several | Oval or rod, often bent or swelling | A single polar flagellum | Abundant | New type |

[1]Int. J. Syst. Bacteriol. 25:371–376 (1975).

With respect to the various genera in the family Actinoplanaceae, the genus Actinoplanes, which includes seven species, resembles strain C677-91 in the shape of sporangia but differs in the arrangement and number of spores in a sporangium and the type of flagellation. The genus Spirillospora and strain C677-91 have several common characteristics such as the shape of sporangia and sporangiospores, the type of flagellation and the

TABLE VI

| | Carbohydrate composition of cell wall | | | | | |
|---|---|---|---|---|---|---|
| | Arabinose | Galactose | Glucose | Mannose | Rhamnose | Glucosamine |
| Strain C677-91 | – | +++ | TR* | +++ | + | + |
| Nocardia corallina | +++ | +++ | – | + | – | + |
| Streptomyces fradiae | – | TR | TR | TR | – | +++ |
| S. antimycoticus | – | TR | TR | TR | – | +++ |
| S. tenebrarius | – | +++ | TR | + | + | +++ |

*trace

TAXONOMY

The actinomycetes strain C677-91 produced clusters and sclerotia in the aerial mycelium which were mor- aerial mycelium formation, but they differ in the arrangement and number of spores in a sporangium. The genus Streptosporangium is similar to C677-91 in the aerial mycelium formation but differs from the latter in many other characteristics listed in Table VII. The genus *Amorphosporangium* is similar to C677-91 in the shape of sporangiospores but differs in the flagellation and the aerial mycelium formation. The genus *Ampullariella* resembles C677-91 in the shape of sporangiospores but differs in the shape of sporangia, the arrangement of spores in a sporangium, the flagellation and the aerial mycelium formation. The genus *Pilimelia* resembles C677-91 in the shape of sporangiospores and the flagellation but differs in the arrangement and number of spores in a sporangium and the aerial mycelium formation. The genus *Dactylosporangium* is similar to C677-91 in the arrangement and number of spores in a sporangium, but differs in the aerial mycelium formation and the type of flaggelation. The genus Kitasatoa is similar to C677-91 in the flagellation and the aerial mycelium formation, but differs in the shape of sporangia and the arrangement of spores in a sporangium and the shape of sporangiospores. Strain C677-91 has a meso-DAP, galactose, mannose and rhamnose as major distinct components of the cell-wall, but does not have LL-DAP, glycine and arabinose. The genera in family *Actinoplanaceae* with exceptions of *Spirillospora* and *Streptosporangium* have glycine as one of the diagnostic cell-wall components. The cell wall composition of strain C677-91 differs from *Spirillospora* and *Streptosporangium* (both cell-wall type III) in the presence of galactose.

*Streptomyces sclerogranulatus* [J. Antibiotics 22: 590–596 (1969)] resembles strain C677-91 in the formation of both cluster and sclerotium. Although no description is available concerning its cell-wall composition and sporangium formation, *S. sclerogranulatus* is differentiated from strain C677-91 in its whitish aerial mycelium production on various media, the lack of thermoduric property, and its positive utilization of xylose, raffinose, mannitol and inositol.

The species most similar to strain C677-91 appears to be *Streptomyces tenebrarius* A.T.C.C. 17920 (Antimicrobial Agents and Chemotherapy — 1967:324–331). They have several important characteristics in common, such as cluster and sclerotium formation, and the carbohydrate utilization pattern except for inositol. The thermoduric property and the antibiotics produced are also similar. The cell-wall components of *S. tenebrarius* A.T.C.C. 17920 were analyzed comparatively with strain C677-91 to reveal a unique cell-wall composition very similar to that of C677-91, hence quite unusual as a *Streptomyces*. *S. tenebrarius* A.T.C.C. 17920, as its species name implies, is light-sensitive and produces no aerial mycelium under fluorescent lamps. Strain C677-91, as well as two other strains of C801-104 and D251-1, grew well with abundant aerial mycelia under the same conditions. Strain C677-91 also differs from *S. tenebrarius* A.T.C.C. 17920 in the lack of red soluble pigment and negative utilization of inositol. Higgens and Kastner (Antimicrobial Agents and Chemotherapy — 1967:324–331) described an asporogenous variant of *S. tenebrarius* (A.T.C.C. 17921), which is reported to be *Nocardia*-like in morphology showing the fragmentation of vegetative mycelium, and hence the variant A.T.C.C. 17921 is also different from strain C677-91. An additional difference was also noted in the NaCl tolerance: strain C677-91 did not grow at the NaCl concentration of 7% while the two strains of *S. tenebrarius* (A.T.C.C. 17920 and A.T.C.C. 17921) gave growth at 8% NaCl medium (but not at 10%) in our experiments. Furthermore, the sporangium was not found in the two strains of *S. tenebrarius* which therefore should be taxonomically differentiated from strain C677-91.

In view of the morphological, cultural and physiological characteristics as well as the cell-wall composition of strain C677-91, it is proposed that a new genus *Streptoalloteichus* be created under family *Actinoplanaceae* in order to distinguish the sporangium-forming actinomycetes strains showing streptomyces-like morphology but with the unusual cell-wall composition of strain C677-91-type: meso-DAP, alanine and glutamic acid as major amino acids, and galactose, mannose and rhamnose as diagnostic nertural sugars. The genus epithet *Streptoalloteichus* means a *Streptomyceslike* organism with unusual cell-wall composition (Greek, allo=altered, teichus=wall).

It is also proposed that strain C677-91 be designated *Streptoalloteichus hindustanus* gen. nov. and sp. nov., because the organism was isolated from soil collected in the northern part of India.

In addition to strain C677-91, two other strains of *Streptoalloteichus hindustanus* designated C108-104 and D251-1 have been obtained from Indian soil samples and found to produce the same aminoglycoside antibiotics as strain C677-91. The strains C677-91, C108-104 and D251-1 show identical characteristics in cell-wall composition, carbohydrate utilization pattern, antibiotic production and in substantially all of the cultural and morphological properties. Minor differences were observed among these strains in the characteristics of aerial mycelium when cultured on tyrosine agar (ISP No. 7) as indicated below:

| Strain | Characteristics of Aerial Mycelium |
|---|---|
| C677-91 | cottony, white later light pinkish yellow |
| C801-104 | velvety, light pinkish beige |
| D251-1 | velvety, white later pale yellowish beige |

From a taxonomical viewpoint, the differences among the three strains are insignificant and all of the strains should thus be placed in the same species, *Streptoalloteichus hindustanus* gen. nov. and sp. nov.

Although this invention is described in detail with particular reference to the newly found organisms *Streptoalloteichus hindustranus* strain C677-91 (A.T.C.C. 31217), strain C801-104 (A.T.C.C. 31218) and strain D251-1 (A.T.C.C. 31219), it is to be understood that the process of the invention is not limited to the particular microorganisms fully described by the characteristics described above. It is intended that this invention also include other strains or mutants of the said microorganisms which produce the same complex or mixture of aminoglycoside antibiotics. Such other strains or mutants can be produced by procedures well known in the art, e.g. by subjecting the novel microorganisms to X-ray or ultraviolet radiation, nitrogen mustard, phage exposure, and the like.

PREPARATION OF THE ANTIBIOTICS

According to the present invention, an aminoglycoside mixture comprising apramycin and nebramycin factor V' (in admixture with the co-produced aminoglycosides neamine, nebramine and nebramycin factor IV) is produced by cultivating a strain of *Streptoallotei-*

*chus hindustanus* having the identifying characteristics of A.T.C.C. 31217, 31218 or 31219 under submerged aerobic conditions in an aqueous nutrient medium containing assimilable sources of carbon and nitrogen until the desired aminoglycoside mixture is produced in the culture medium.

The organism is grown in a nutrient medium containing an assimilable carbon source, for example, an assimilable carbohydrate. Examples of suitable carbon sources include glucose, galactose, fructose, mannose, maltose and glycerol. The nutrient medium should also contain an assimilable nitrogen source such as, for example, fish meal, soybean meal, corn steep liquor, peptones, meat extract, peanut flour, yeast extract or ammonium salts. Nutrient inorganic salts may also be advantageously incorporated in the culture medium, and such salts may comprise any of the usual salts capable of providing sodium, potassium, ammonium, calcium, phosphate, sulfate, chloride, bromide, nitrate, carbonate or like ions. Trace elements such as copper, manganese, iron, zinc, etc. are added to the medium if desired or may be supplied as impurities of other constituents of the media.

Production of the aminoglycoside mixture may be effected at any temperature conducive to satisfactory growth of the organism, e.g. 25°-50°C., and is conveniently carried out at a temperature of about 28°-30°C. Ordinarily, optimum production of the antibiotics is obtained in about 2-5 days. A neutral or near neutral initial pH, e.g. pH 6-7, is preferably used for the medium.

Submerged aerobic culture conditions are the conditions of choice for production of the antibiotic mixture. For preparation of relatively small amounts, shake flasks and surface culture can be employed, but for the preparation of large amounts, submerged aerobic culture in sterile tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. The fermentation medium in which the vegetative inoculum is produced can be either the same as or different from the medium utilized for the large scale production of the antibiotics.

Production of the desired antibiotic mixture can readily be followed during the course of fermentation by the paper disc-agar diffusion assay method using *Bacillus subtilis* PCI-219 as a test microorganism and nebramycin factor V' as an assay standard.

ISOLATION OF THE ANTIBIOTIC MIXTURE

After optimum broth potency has been obtained (as determined by the above-described assay), the mycelium and undissolved residues are separated from the fermentation broth by conventional means such as filtration or centrifugation. The antibiotic mixture obtained during fermentation may then be removed from the aqueous broth by employing standard isolation techniques such as chromatography on ion exchange resins or other solid adsorbents. In a preferred recovery procedure, the fermentation broth is filtered at pH2, the filtrate is adjusted to pH 7 and the neutralized filtrate adsorbed on a cation exchange resin, preferably a weakly acidic cation exchange resin of the type sold commerically under the tradenames "Amberlite IRC-50" or CG-50", and most preferably a weakly acidic cation exchange resin of the Amberlite IRC-50 type in the ammonium cycle. The antibiotic mixture is eluted from the resin with dilute base such as 0.5N $NH_4OH$, and the active eluates are combined, concentrated in vacuo and lyophilized to give a solid mixture of antibiotics comprising the desired apramycin and nebramycin factor V' components as well as neamine, nebramine and nebranycin factor IV. The recovered mixture of antibiotics may then be separated into its aminoglycoside components, including especially the components apramycin and nebramycin factor V', by art-recognized techniques or, alternatively, the mixture may first be subjected to a base catalyzed hydrolysis step before separation so as to convert the nebramycin factor V' component to tobramycin.

PREPARATION OF TOBRAMYCIN

As with the known nebramycin-producing organism *Streptomyces tenebrarius*, the novel microorganisms of the present invention do not produce tobramycin directly in the fermentation step. Tobramycin can, however, be formed from the fermentation-produced nebramycin factor V' component by known methods such as described in J. Antibiotics 26(12): 745-751 (1973). The tobramycin conversion step may be performed either before or after the fermentation-produced aminoglycoside mixture is separated into the individual antibiotic components.

In a preferred procedure for preparing tobramycin according to the present invention, a nebramycin factor V'-producing strain of *Streptoalloteichus hinudstanus* having the identifying characteristics of A.T.C.C. 31217, 31218 or 31219 is fermented as described above to produce an aminoglycoside mixture containing nebramycin factor V', the so-produced aminoglycoside mixture is recovered from the culture medium, the aminoglycoside mixture is subjected to base catalyzed hydrolysis as by treatment with alkali metal hydroxide or by chromatography over a strongly basic anion exchange resin to convert the nebramycin factor V' component thereof to tobramycin and the tobramycin is then separated and recovered from the resulting aminoglycoside mixture by conventional methods, e.g. by the chromatographic separation methods discussed below. The hydrolysis of nebramycin factor V' to tobramycin is most preferably carried out by chromatography of an aqueous solution of the antibiotic mixture (after recovery from the fermentation broth) over a strongly basic anion exchange resin, preferably a strongly basic anion exchange resin in the hydroxyl cycle and most preferably a resin of the type sold commercially under the tradename "Dowex 1×2($OH^-$)". The active effluents from the resin are pooled, concentrated in vacuo and lyophilized to give an antibiotic solid comprising the desired tobramycin in admixture with apramycin, neamine, nebramine, and nebramycin factors IV and V'.

An alternative procedure for preparing tobramycin according to the present invention involves preparing an aminoglycoside mixture containing nebramycin factor V' by fermenting as described above a nebramycin factor V'-producing strain of *Streptoalloteichus hindustanus* having the identifying characteristics of A.T.C.C. 31217, 31218 or 31219, recovering the so-produced mixture from the culture medium, separating nebramycin factor V' from the antibiotic mixture, e.g. by the chromatographic separation methods disclosed below, and converting the nebramycin factor V' to tobramycin by base catalyzed hydrolysis. The hydrolysis of nebramycin factor V' may be accomplished by known methods, e.g. by treatment with an alkali metal hydroxide at 100° C. or by chromatography of an aqueous solution of nebramycin factor V' over a strongly basic anion exchange resin, e.g. a resin of the Dowex 1×2 type in the hydroxyl cycle.

SEPARATION OF THE ANTIBIOTICS

Separation of the aminoglycoside antibiotic components from the antibiotic mixture produced during the fermentation process (or resulting from the base catalyzed hydrolysis of the antibiotic mixture produced by fermentation) may be achieved by various techniques known in the art. A preferred separation procedure employs chromatography of an aqueous solution of the aminoglycoside antibiotic mixture over a cation exchange resin, preferably a weakly acidic cation exchange resin of the type sold commercially under the tradenames "Amberlite IRC-50" or "CG-50" and most preferably a weakly acidic cation exchange resin of the type sold commercially as Amberlite CG-50 in the ammonium cycle. The adsorbed antibiotic mixture is then subjected to a stepwise elution procedure using a weak base as the eluant. In a particularly preferred method, an aqueous solution of the antibiotic mixture recovered from the fermentation medium is adsorbed on Amberlite CG-50 ($NH_4^+$) and eluted with aqueous ammonium hydroxide of concentrations varying successively from N/20 to N/4. Using this procedure, apramycin appears in the early fractions of eluate followed in order by nebramycin factor V', neamine, tobramycin (if the base catalyzed hydrolysis step has been performed) and nebramine. The eluant fractions containing the same components are pooled concentrated and lyophilized to give the individual aminoglycoside antibiotics.

Physico-chemical analyses of the aminoglycoside antibiotic components produced according to the present invention or of derivatives of these components conclusively establish that they are in fact the previously known antibiotics apramycin, nebramycin factor V', tobramycin, neamine, nebramine and nebramycin factor IV (see Experimental Section below).

The apramycin, tobramycin and nebramycin factor V' antibiotics produced according to the present invention may be converted to pharmaceutically acceptable acid addition salts by conventional methods such as described in U.S. Pat. Nos. 3,691,279 and 3,853,709.

The following examples are offered only for the purposes of illustrating the present invention and are not intended to limit same in any respect. "Amberlite" is a registered trademark of the Rohm and Haas Company, Philadelphia, Pennsylvania. Amberlite IRC-50 and CG-50 are tradenames for weakly acidic cation exchange resins of a carboxylic-polymethacrylic type. "Dowex 1×2 ($OH^-$)" is the tradename of the Dow Chemical Company, Midland, Michigan, for a strongly basic anion exchange resin made from styrene-divinylbenzene copolymers.

EXAMPLES

EXAMPLE 1 — FERMENTATION

A. A well-grown agar slant of *Streptoalloteichus hindustanus* strain C677–91 was used to inoculate vegetative medium (pH 7.0 before sterilization) having the following composition:

Glycerol: 2%
*Pharmamedia: 1%
Corn Steep Liquor: 1%
$(NH_4)_2SO_4$: 0.3%
$ZnSO_4 \cdot 7H_2O$: 0.003%
$CaCO_3$: 0.4%.

* an industrial grade of cottonseed flour produced by Traders Oil Mill Company, Fort Worth, Texas.

The seed culture was incubated at 28° C. for 2 days on a rotary shaker running at 250 rpm. About 2 ml. of the seed culture was transferred to 100 ml. of fermentation medium (pH 7.0 before sterilization) in a 500 ml. Erlenmeyer flask, said fermentation medium having the composition Soluble Starch: 2%
Corn Meal: 2%
Pharmamedia: 1%
NaCl: 0.3%
$CaCO_3$: 0.2%. Antibiotic production reached a maximum after 3 to 5 days shaking at 28° C. A maximum potency of about 200 mcg./ml. was reached on the fourth day.

B. Fermentation with strain C677–91 was also carried out in 10 liter jar fermentors. The seed and fermentation media used were the same as those employed in the shake-flask procedure described above. The inoculum size was 1–2% and the fermentors were operated at 30° C. with stirring at 200–250 rpm. The peak antibiotic potency of 150–300 mcg./ml. was obtained in about 60–70 hours.

C. Fermentation with *Streptoalloteichus hindustanus* strain C801–104 was carried out by the shake-flask procedure of step A except that both the seed medium and fermentation medium had the composition:

Glycerol: 2%
Pharmamedia: 1%
Corn Steep Liquor: 1%
$(NH_4)_2SO_4$: 0.3%
$ZnSO_4 \cdot 7H_2O$: 0.003%
$CaCO_3$: 0.4%.

A peak potency of 225 mcg./ml. was obtained after 4 days.

D. Fermentation with *Streptoalloteichus hindustanus* strain D251–1 was carried out by the shake-flask procedure of step A except that both the seed medium and fermentation medium had the composition:

Glycerol: 2%
Pharmamedia: 1%
Corn Steep Liquor: 1%
$(NH_4)_2SO_4$: 0.3%
$ZnSO_4 \cdot 7H_2O$: 0.003%
$CaCO_3$: 0.4%.

A peak potency of 200 mcg./ml. was obtained after three days.

EXAMPLE 2

Recovery of Antibiotic Mixture

Fermentation broth obtained according to the procedures of Example 1 was filtered at pH 2 with filter aid. The filtrate (ca 4L) was adjusted to pH 7.0 and applied to a column of Amberlite IRC-50 ($NH_4^+$). The column was washed with water and then developed with N/2 $NH_4OH$. The active eluates were combined, concentrated in vacuo and lyophilized to give crude antibiotic solid (1.9 g., 150 mcg./mg.). Subsequent chromatography of the solid antibiotic showed it to be a mixture of apramycin, nebramycin factor V', neamine, nebramine and nebramycin factor IV.

EXAMPLE 3

Preparation of Tobramycin-containing Mixture

The solid mixture prepared in Example 2 was dissolved in water and passed through a column of Dowex 1×2 (OH⁻). The active effluents were pooled, concentrated in vacuo and lyophilized to yield a white powder (0.4 g., 600 mcg./ml.). Subsequent chromatographic separation of this powder showed it to be a mixture of apramycin, nebramycin factor V', tobramycin, neamine, nebramine and nebramycin factor IV.

EXAMPLE 4

Separation of the Antibiotic Components

An aqueous solution of the antibiotic mixture obtained in Example 3 was applied to a column of Amberlite CG-50 ($NH_4^+$) and the column was developed successively with N/20, N/10, N/8 and N/4 $NH_4OH$. Each 15 ml. portion of the eluate was collected from fraction collector and examined by ninhydrin reagent and bioassay. Component $B_1$ (apramycin) was eluted first followed in order by $B_2$ (nebramycin factor IV), $A_1$ (nebramycin factor V'), $A_2$ (neamine), $A_3$ (tobramycin) and $A_4$ (nebramine). Each component was further purified by rechromatography on a column of Amberlite CG-50 resin ($NH_4^+$). The distribution of antibiotics from the column is shown below:

| Component | Eluant | Tube No. | Yield (mg.) | Indentification |
|---|---|---|---|---|
| $B_1$ | N/20 $NH_4OH$ | 192–210 | 49 | Nebramycin factor II (apramycin) |
| $B_2$ | N/10 $NH_4OH$ | 367–402 | 9 | Nebramycin factor IV |
| $A_1$ | N/10 $NH_4OH$ | 507–543 | 21 | Nebramycin factor V' |
| $A_2$ | N/8 $NH_4OH$ | 651–706 | 12 | Neamine |
| *$A_3$ | N/4 $NH_4OH$ | 798–814 | 16 | Nebramycin factor VI (tobramycin) |
| $A_4$ | N/4 $NH_4OH$ | 831–854 | 11 | Nebramine |

*Component $A_3$ was not obtained when the Dowex 1×2 resin process described in Example 3 was omitted in preparation of the antibiotic mixture.

CHARACTERIZATION OF COMPONENTS AND IDENTIFICATION WITH KNOWN ANTIBIOTICS

Component $A_1$ produced in Example 4 was isolated as a carbonate salt and analyzed as $C_{19}H_{38}N_6O_{10} \cdot H_2CO_3$.
Anal. Calc'd.: C, 41.95; H, 7.04; N, 14.68. Found: C, 41.96; H, 7.11; N, 14.58.

The UV spectrum of component $A_1$ exhibited only end absorption and the IR spectrum showed a characteristic strong absorption band at 1710 cm⁻¹. The NMR spectrum in $DCl/D_2O$ indicated the presence of two methylene groups at around $\delta 1.7$–2.7 ppm and two anomeric protons at $\delta 5.18(d)$ and $5.86(d)$ ppm.

Alkaline hydrolysis of component $A_1$ in 0.5N NaOH (100° C., 1 hr.) gave component $A_3$ which was identified as tobramycin. Treatment of component $A_1$ in $Ba(OH)_2$ solution (100° C., 4 hr.) yielded a nearly equimolar amount of ammonia and barium carbonate, supporting the structure of 6''-O-carbamoyltobramycin (nebramycin factor V') for component $A_1$.

Components $A_2$ and $A_4$ were identified as neamine and nebramine, respectively, by direct comparison with authentic samples.

Component $B_1$ was analyzed as $C_{21}H_{41}N_5O_{11}$. Anal. Calc'd.: C, 46.74; H, 7.66; H, 12.93. Found: C, 46.22; H, 7.60; H, 12.79.

The NMR spectrum of component $B_1$ indicated the presence of one N-$CH_3$ group at $\delta 2.9(s)$ ppm and two anomeric protons at $\delta 5.30(d)$, $\delta 5.58(d)$ and $\delta 5.85(d)$ ppm. Component $B_1$ was identified as apramycin by TLC, IR and NMR spectra.

Alkaline hydrolysis of component $B_2$ in 0.5N NaOH gave a bioactive degradation product which was identified as kanamycin B. When heated in a $Ba(OH)_2$ solution, component $B_2$ yielded nearly quantitative amounts of ammonia and barium carbonate. Component $B_2$ was identified as nebramycin factor IV (6''-O-carbamoyl-kanamycin B) by comparison with an authentic sample.

The $R_f$ values for each of the components (determined by silica gel thin layer chromatography) are shown in the table below along with those of authentic samples.

| Compound | TLC System* | | |
|---|---|---|---|
| | S-117 | S-118 | S-119 |
| Component $A_1$ | 0.58 | | 0.25 |
| Component $A_2$ | 0.50 | 0.30 | |
| Component $A_3$ | 0.53 | 0.40 | |
| Component $A_4$ | 0.61 | | |
| Component $B_1$ | 0.43 | | |
| Component $B_2$ | 0.48 | | 0.18 |
| Neamine | 0.48 | 0.30 | |
| Nebramine | 0.61 | | |
| Apramycin | 0.43 | | |
| Nebramycin factor IV | 0.48 | | 0.18 |
| Nebramycin factor V' | 0.58 | | 0.25 |
| Tobramycin | 0.53 | 0.40 | |

*S-117: $CHCl_3$–$CH_3OH$–conc. $NH_4OH$ (1:3:2)
S-118: $CHCl_3$–$CH_3OH$–conc. $NH_4OH$ (1:2:1)
S-119: Methyl ethyl ketone-t-butyl alcohol –$CH_3OH$– 7.5N $NH_4OH$ (16:3:3:12).

We claim:

1. A microbiological process for the preparation of an aminoglycoside antibiotic mixture comprising apramycin and nebramycin factor V' which comprises cultivating a strain of Streptoalloteichus hindustanus having the identifying characteristics of A.T.C.C. 31217, 31218 or 31219 under submerged aerobic conditions in an aqueous medium containing assimilable sources of carbon and nitrogen until a substantial amount of said antibiotic mixture is produced by said organism in said culture medium.

2. The process of claim 1 wherein the organism is Streptoalloteichus hindustanus A.T.C.C. 31217.

3. The process of claim 1 wherein the organism is Streptoalloteichus hindustanus A.T.C.C. 31218.

4. The process of claim 1 wherein the organism is Streptoalloteichus hindustanus A.T.C.C. 31219.

5. The process of claim 1 which includes the additional step of recovering the antibiotic mixture from the culture medium.

6. A microbiological process for preparation of apramycin which comprises
   a. culturing an apramycin-producing strain of Streptoalloteichus hindustanus having the identifying characteristics of A.T.C.C. 31217, 31218 or 31219 under submerged aerobic conditions in an aqueous medium containing assimilable sources of carbon and nitrogen until a substantial amount of antibiotic activity is produced by said organism in said culture medium;
   b. recovering the antibiotic mixture produced in step (a) from the culture medium; and c. separating apramycin from said antibiotic mixture by chromatography over a cation exchange resin.

7. The process of claim 6 wherein the organism is *Streptoalloteichus hindustanus* A.T.C.C. 31217.

8. The process of claim 6 wherein the organism is *Streptoalloteichus hindustanus* A.T.C.C. 31218.

9. The process of claim 6 wherein the organism is *Streptoalloteichus hindustanus* A.T.C.C. 31219.

10. A microbiological process for the preparation of nebramycin factor V' which comprises
 a. cultivating a nebramycin factor V'-producing strain of *Streptoalloteichus hindustanus* having the identifying characteristics of A.T.C.C. 31217, 31218 or 31219 under submerged aerobic conditions in an aqueous medium containing assimilable sources of carbon and nitrogen until a substantial amount of antibiotic activity is produced by said organism in said culture medium;
 b. recovering the antibiotic mixture produced in step (a) from the culture medium; and
 c. separating nebramycin factor V' from said antibiotic mixture by chromatography over a cation exchange resin.

11. The process of claim 10 wherein the organism is *Streptoalloteichus hindustanus* A.T.C.C. 31217.

12. The process of claim 10 wherein the organism is *Streptoalloteichus hindustanus* A.T.C.C. 31218.

13. The process of claim 10 wherein the organism is *Streptoalloteichus hindustanus* A.T.C.C. 31219.

14. A process for the preparation of tobramycin which comprises
 a. culturing a nebramycin factor V'-producing strain of *Streptoalloteichus hindustanus* having the identifying characteristics of A.T.C.C. 31217, 31218 or 31219 under submerged aerobic conditions in an aqueous medium containing assimilable sources of carbon and nitrogen until a substantial amount of antibiotic activity is produced by said organism in said culture medium;
 b. recovering the antibiotic mixture produced in step (a) from the culture medium;
 c. subjecting said antibiotic mixture to base catalyzed hydrolysis to convert the nebramycin factor V' component to tobramycin; and
 d. separating tobramycin from the antibiotic mixture of step (c) by chromatography over a cation exchange resin.

15. The process of claim 14 wherein the organism is *Streptoalloteichus hindustanus* A.T.C.C. 31217.

16. The process of claim 14 wherein the organism is *Streptoalloteichus hindustanus* A.T.C.C. 31218.

17. The process of claim 14 wherein the organism is *Streptoalloteichus hindustanus* A.T.C.C. 31219.

18. The process of claim 14 wherein step (c) is effected by chromatography over a strongly basic anion exchange resin.

19. A process for the preparation of tobramycin which comprises
 a. culturing a nebramycin V'-producing strain of *Streptoalloteichus hindustanus* having the identifying characteristics of A.T.C.C. 31217, 31218 or 31219 under submerged aerobic conditions in an aqueous medium containing assimilable sources of carbon and nitrogen until a substantial amount of antibiotic activity is produced by said organism in said culture medium;
 b. recovering the antibiotic mixture produced in step (a) from the culture medium;
 c. separating nebramycin factor V' from said antibiotic mixture by chromatography over a cation exchange resin; and
 d. converting nebramycin factor V' to tobramycin by base catalyzed hydrolysis.

20. The process of claim 19 wherein the organism is *Streptoalloteichus hindustanus* A.T.C.C. 31217.

21. The process of claim 19 wherein the organism is *Streptoalloteichus hindustanus* A.T.C.C. 31218.

22. The process of claim 19 wherein the organism is *Streptoalloteichus hindustanus* A.T.C.C. 31219.

* * * * *